United States Patent
Washiyama et al.

(10) Patent No.: US 7,264,966 B2
(45) Date of Patent: Sep. 4, 2007

(54) METHOD OF ISOLATING CELL OR SAMPLE TO BE ANALYZED IN CELL

(75) Inventors: Kazuo Washiyama, Niigata (JP); Shinichi Dosaka, Tsukui-gun (JP)

(73) Assignee: Olympus Optical Co., Ltd., Tokyo (JP)

( * ) Notice: Subject to any disclaimer, the term of this patent is extended or adjusted under 35 U.S.C. 154(b) by 431 days.

(21) Appl. No.: 10/348,198

(22) Filed: Jan. 21, 2003

(65) Prior Publication Data

US 2004/0043392 A1    Mar. 4, 2004

(30) Foreign Application Priority Data

Jan. 23, 2002    (JP) .............................. 2002-014643

(51) Int. Cl.
| C12N 5/00 | (2006.01) |
| C12N 5/02 | (2006.01) |
| C12N 5/06 | (2006.01) |

(52) U.S. Cl. ...................................... 435/325; 435/378
(58) Field of Classification Search ................ 435/325, 435/6, 1.1, 378
See application file for complete search history.

(56) References Cited

U.S. PATENT DOCUMENTS

| 5,585,116 A | * | 12/1996 | Boniface et al. ............ 424/549 |
| 5,859,699 A | | 1/1999 | Baer et al. |
| 5,998,129 A | | 12/1999 | Schütze et al. |
| 6,040,139 A | | 3/2000 | Bova |
| 6,100,051 A | | 8/2000 | Goldstein et al. |
| 6,316,234 B1 | | 11/2001 | Bova |
| 6,455,309 B2 | * | 9/2002 | Stone ......................... 435/378 |
| 2002/0048747 A1 | | 4/2002 | Ganser |
| 2002/0056345 A1 | | 5/2002 | Ganser et al. |

FOREIGN PATENT DOCUMENTS

JP    2000-266649 A    9/2000

* cited by examiner

*Primary Examiner*—Ruth A Davis
(74) *Attorney, Agent, or Firm*—Frishauf, Holtz, Goodman & Chick, P.C.

(57) ABSTRACT

There is disclosed a method of irradiating a specimen which is laid on a substrate and which includes a cell with a laser beam to remove an unnecessary specimen portion other than a cell portion from the substrate, next inserting the cell portion into one opening in a cylindrical member to dispose the cylindrical member onto the substrate, next injecting a stripping agent into a container formed by the substrate and cylindrical member to strip the cell portion from the substrate, and sampling the cell portion which floats in the stripping agent.

14 Claims, 5 Drawing Sheets

METHOD OF ISOLATING CELL OR SAMPLE TO BE ANALYZED IN CELL

CROSS-REFERENCE TO RELATED APPLICATIONS

This application is based upon and claims the benefit of priority from the prior Japanese Patent Application No. 2002-14643, Jan. 23, 2002, the entire contents of which are incorporated herein by reference.

BACKGROUND OF THE INVENTION

1. Field of the Invention

The present invention relates to a method comprising: selecting a specific cell or cells to be analyzed from a specimen on a substrate; and isolating the cell or cells to be analyzed.

2. Description of the Related Art

At present, a research to analyze a function of a gene has been a matter of greatest concern. In the research of analysis of the gene function, cells are acquired from a specimen. A sample for the analysis of the gene function is directly sampled from the cells. Various types of an apparatus for sampling the cells or sample have been developed and used.

Various cell sampling methods for sampling the cells from a slice of a specimen will be described.

(1) A slice of a specimen is fixed onto a thin film plate. The slice of the specimen includes, for example, the cells to be sampled for the analysis of the functions of the gene. The thin film plate is irradiated with a laser beam of an ultraviolet wavelength region (UV laser beam) along a contour of the cells. Thereby, the cells to be sampled in the specimen are cut/separated together with the thin film plate.

Next, a cut/separated portion is irradiated with the UV laser beam out of focus with respect to the thin film plate. Thereby, the cut/separated portion in the specimen is flied. As a result, the cells to be sampled are acquired.

(2) A transparent cap for sampling to which a transfer film is attached is used. The transparent cap is laid on the specimen which has the cells to be sampled. The portion including the cells to be sampled in the specimen are irradiated with an IR laser beam through the transparent cap. Thereby, the cell portion to be sampled adheres to a transfer film surface.

(3) The specimen is attached onto the film. The surface to which the specimen is attached on the film is turned downwards. In this state, the UV laser beam is emitted along the contour of the cells from above. Thereby, the periphery of the cells to be sampled are cut off.

Next, the film is irradiated with the UV laser beam. Thereby, the cells to be sampled are detached from the film and dropped into a tray which is set below.

However, the method (1) comprises: cutting/separating the cells to be sampled together with the thin film plate; and subsequently irradiating the cut/separated portion with the UV laser beam out of focus to fly the portion. Therefore, a place of the cells to be sampled are not known. The cells are lost in many cases. Moreover, it is also expected that properties of the cells are changed by the UV laser beam.

Moreover, foreign particles such as dust are easily mixed in the sampled cells. It is necessary to fix the specimen onto the thin film plate beforehand. Therefore, the sampling operation of the cells requires troubles and is laborious.

The method (2) comprises: irradiating the cells to be sampled in the specimen with the IR laser beam transmitted through the transparent cap. Therefore, a spot diameter of the IR laser beam with which the cells to be sampled are irradiated cannot be reduced. The spot diameter of the IR laser beam is also sometimes larger than the size of the cells to be sampled. When the cells are irradiated with the laser beam having the spot diameter larger than the size of the cells to be sampled, together with the cells to be sampled, unnecessary surrounding cells also stick to the transfer film surface. For example, to sample a micro cell of five microns or less with a spot diameter of ten microns, the surrounding unnecessary cells also stick to the transfer film surface.

Since the cells to be sampled are attached to the transfer film surface, depending on a dry degree of the cells, the cells cannot well stick to the transfer film surface, and the cells cannot sometimes be sampled. It is impossible to sample the cells in a wet state. The sticking of the cells to the transfer film surface is influenced by conditions of the cells such as the dry degree of the cells. In other words, the capability of sampling the cells is limited by the conditions of the cells.

With an increase of the output of the IR laser beam with which the specimen is irradiated, an efficiency of attaching the cell portion to the transfer film surface to sample the cells is improved. On the other hand, when the output of the IR laser beam is increased, the cells burn.

The method (3) comprises: dropping the cell portion sampled by the irradiation with the UV laser beam down to the tray which is set below. Therefore, the place of the cells to be sampled is not known. Moreover, the foreign particles such as dust are easily mixed in the acquired cells. It is also expected that the properties of the cells are changed by the UV laser beam.

The above-described problems are summarized as follows.

(a) It takes much time to sample the cells to be sampled. Additionally, the cells are easily lost at a sampling time.

(b) It is difficult to acquire small cells. The cells which can be sampled are limited by a dry state of the specimen.

(c) It is impossible to acquire a large amount of cells having sufficient qualities in a short time by causes such as the change of the properties of the cells by the UV laser beam.

BRIEF SUMMARY OF THE INVENTION

According to a main viewpoint of the present invention, there is provided a method of isolating a cell or a group of cells, comprising: irradiating a specimen which is laid on a substrate and which includes the cells with a laser beam to remove an unnecessary specimen portion other than a necessary cell portion from the substrate; using a cylindrical member including openings in opposite ends; inserting the cell portion into one opening in the cylindrical member and disposing the cylindrical member onto the substrate; injecting a stripping agent into a container formed by the substrate and cylindrical member to strip the cell portion from the substrate; and sampling the cell portion which is floated in the stripping agent.

According to the main viewpoint of the present invention, there is provided a method of isolating a cell or a group of cells or a sample to be analyzed in the cells, comprising: irradiating a specimen which is laid on a substrate and which includes the cells with a laser beam to remove an unnecessary specimen portion other than a necessary cell portion from the substrate; using a cylindrical member including openings in opposite ends; inserting the necessary cell portion into one opening in the cylindrical member and disposing the cylindrical member onto the substrate; injecting a solution for eluting the sample existing in the cells into a container formed by the substrate and cylindrical member; and sampling the sample eluted in the solution.

According to the main viewpoint of the present invention, there is provided a method of isolating a cell or a group of cells, comprising: irradiating a specimen which is laid on a substrate and which includes the cells with a laser beam to change properties of an unnecessary specimen portion other than a necessary cell portion; using a cylindrical member including openings in opposite ends; inserting the necessary cell portion into one opening in the cylindrical member and disposing the cylindrical member onto the substrate; injecting a stripping agent into a container formed by the substrate and cylindrical member to strip the necessary cell portion from the substrate; and sampling the necessary cell portion which floats in the stripping agent.

According to the main viewpoint of the present invention, there is provided a method of isolating a cell or a group of cells or a sample to be analyzed in the cells, comprising: irradiating a specimen which is laid on a substrate and which includes the cells with an ultraviolet light to change properties of an unnecessary specimen portion other than a necessary cell portion; using a cylindrical member including openings in opposite ends; inserting the necessary cell portion into one opening in the cylindrical member and disposing the cylindrical member onto the substrate; injecting a stripping agent into a container formed by the substrate and cylindrical member to strip the necessary cell portion from the substrate; and sampling the necessary cell portion which is floated in the stripping agent.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

A first embodiment of the present invention will be described hereinafter with reference to the drawings.

Figure 1:
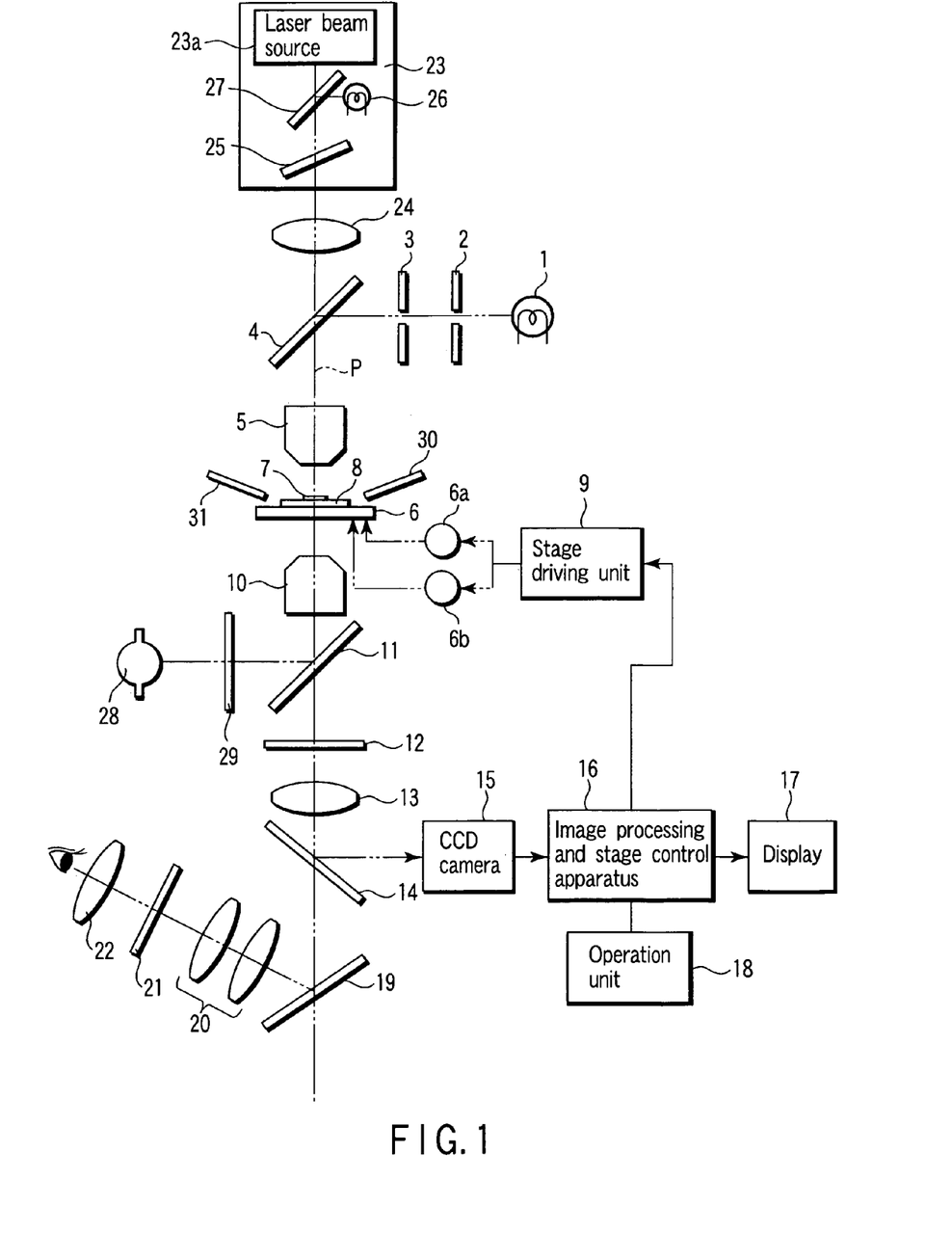
FIG. 1 is a constitution diagram of an inverted microscope for use in a first embodiment of a cell acquiring method of the present invention.

FIG. 1 is a constitution diagram of an inverted microscope for use in a cell acquiring method of the present invention. In a light source for lighting 1, for example, a halogen lamp is used. The light source for lighting 1 outputs visible rays. A view field stop 2, aperture stop 3, and dichroic mirror 4 are disposed on a light path of visible rays outputted from the light source for lighting 1.

The view field stop 2 and aperture stop 3 constitute an optical system of a conventional microscope. The dichroic mirror 4 reflects the visible rays toward a lower part of an optical axis P.

An objective lens for laser 5 is disposed on a reflected light path (optical axis P) of the dichroic mirror 4. The objective lens for laser 5 collects the visible rays outputted from the light source for lighting 1 to irradiate a specimen 7. The objective lens for laser 5 functions as a condenser lens.

A stage 6 is disposed on the reflected light path of the dichroic mirror 4. A slide glass 8 on which the specimen 7 is laid is laid on the stage 6. The stage 6 includes motors 6a, 6b of X and Y directions. The motor 6a of the X direction is driven to move the stage 6 in the X direction. The motor 6b of the Y direction is driven to move the stage 6 in the Y direction. A stage driving unit 9 drives the respective motors 6a, 6b of the X and Y directions.

The specimen 7 is a tissue slice or cultured cells for use, for example, in analyzing a gene function. When a nucleus of the cell is fluori-dyed to observe fluorescence and to acquire the cell, the specimen 7 is applied with fluorescence dyestuff beforehand.

An objective lens for observation 10, dichroic mirror 11, UV barrier filter 12, image forming lens 13, and half mirror 14 are disposed on the optical axis P transmitted through the specimen 7.

A CCD camera 15 is disposed on the reflected light path of the half mirror 14. The CCD camera 15 is disposed in an image forming position of the image forming lens 13 via the half mirror 14. The CCD camera 15 picks up an image formed by the image forming lens 13 to output an image signal.

An image processing and stage control apparatus 16 inputs the image signal outputted from the CCD camera 15, image-processes the image signal to acquire image data, and displays the image data in a display 17.

The image processing and stage control apparatus 16 is connected to operation units 18 such as a keyboard and mouse. The operation unit 18 receives an operation of a movement direction and movement amount of the stage 6 by an observer, and generates this operation command. The image processing and stage control apparatus 16 receives the operation command from the operation unit 18, and transmits a movement control signal of the stage 6 to the stage driving unit 9 in accordance with the operation command.

A mirror 19 is disposed on a transmitted light path of the half mirror 14. Relay lenses 20, UV cut filter 21, and eyepiece lens 22 are disposed on the reflected light path.

On the other hand, a UV laser head 23 is disposed on the optical axis P passed through the objective lens for laser 5 and dichroic mirror 4. A UV image forming lens 24 is disposed on the optical axis p between the UV laser head 23 and dichroic mirror 4.

The UV laser head 23 includes a laser beam source 23a. The UV laser head 23 outputs a laser beam having a wavelength of an ultraviolet region. The laser beam outputted from the UV laser head 23 removes unnecessary cells other than the cell to be sampled among a plurality of cells included in the specimen 7 from the slide glass 8.

Energy of the laser beam outputted from the UV laser head 23 is set to such a degree that the unnecessary cell on the slide glass 8 is removed from the slide glass 8.

The UV laser head 23 includes a variable slit 25 and LED 26. The variable slit 25 includes, for example, a circular or quadrilateral opening. The variable slit 25 can vary the diameter of the opening. The variable slit 25 varies the spot diameter of the laser beam outputted from the UV laser head 23.

The LED 26 outputs an LED light. The LED light is a light having a wavelength of the visible ray, such as a red visible ray.

A dichroic mirror 27 is disposed on the light path of the LED light. The dichroic mirror 27 reflects the LED light outputted from the LED 26 toward the optical axis p of the laser beam outputted from the UV laser head 23.

Thereby, the LED light passes through the dichroic mirror 27 which has a transmission property with respect to the wavelengths of the LED light and UV laser beam, and the same position as the irradiation position of the laser beam is irradiated in the specimen 7. The red LED light with which the specimen 7 is irradiated displays the irradiation position of the laser beam with which the specimen 7 is irradiated.

A light source for fluorescence excitation 28 and UV band pass filter 29 are disposed on the reflected light path of the dichroic mirror 11. The light source for fluorescence excitation 28 is disposed below the stage 6. The light source for fluorescence excitation 28 outputs an ultraviolet light. The light source for fluorescence excitation 28 is, for example, a mercury lamp.

The ultraviolet light outputted from the light source for fluorescence excitation 28 is transmitted through the UV band pass filter 29, and reflected by the dichroic mirror 11, and the specimen 7 is irradiated through the objective lens for observation 10. The ultraviolet light outputted from the light source for fluorescence excitation 28 excites the fluorescence dyestuff applied to the specimen 7 beforehand.

An air blow 30 is disposed obliquely above the stage 6. The air blow 30 sprays air toward the specimen 7 laid on the stage 6. When the unnecessary cells in the specimen 7 is removed from the slide glass 8, a broken piece of the unnecessary cells is generated. The broken piece of the unnecessary cells is blown/flied from the slide glass 8 by the air sprayed by the air blow 30.

An air suction unit 31 is disposed obliquely above the stage 6. The air suction unit 31 is disposed opposite to the air blow 30 via the specimen 7 on the stage 6. The air suction unit 31 sucks air, and sucks the broken pieces of the cells flied by the air spraying of the air blow 30.

Next, a sampling method of the cells existing in the specimen 7 will be described.

The specimen 7 is laid on the slide glass 8. The slide glass 8 is laid on the stage 6.

The light source for lighting 1 outputs the visible ray. The visible ray is passed through the view field stop 2 and aperture stop 3, and reflected by the dichroic mirror 4, and the specimen 7 is irradiated through the objective lens for laser 5. A part of the visible ray with which the specimen 7 is irradiated passes through the specimen 7.

The light passed through the specimen 7 passes through the objective lens for observation 10, is transmitted through the dichroic mirror 11 and UV barrier filter 12, and is formed into the image by the image forming lens 13.

The CCD camera 15 picks up an enlarged image of the specimen 7 formed by the image forming lens 13 via the half mirror 14 to output the image signal.

The image processing and stage control apparatus 16 inputs the image signal outputted from the CCD camera 15, image-processes the image signal to acquire the image data, and displays the image data in the display 17.

Additionally, the image of the specimen 7 formed by the image forming lens 13 is reflected by the mirror 19, and incident upon the eyepiece lens 22 through the relay lenses 20 and UV cut filter 21. The observer sees through the eyepiece lens 22 to visually observe the enlarged image of the specimen 7.

The observer observes the specimen 7 displayed in the display 17 or sees through the eyepiece lens 22 to observe the enlarged image of the specimen 7 and determines the cell to be sampled from the specimen 7.

Figure 2:
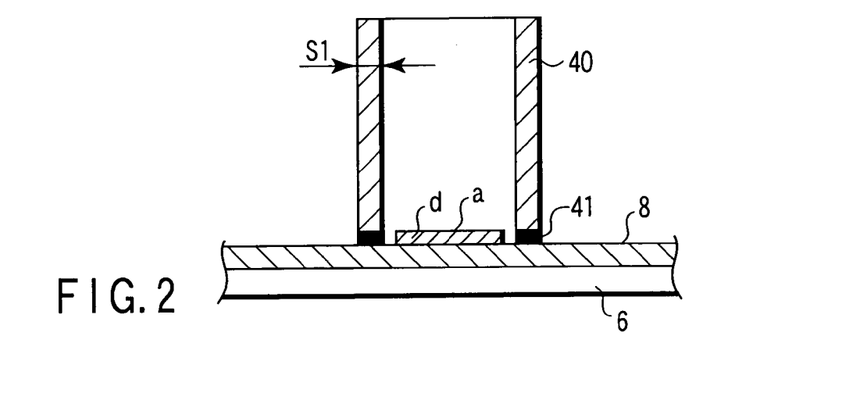
FIG. 2 is a diagram showing a cylindrical member for use in sampling cells in the first embodiment.

To sample cells a from the specimen 7, a cylindrical member 40 shown in FIG. 2 is used. The cylindrical member 40 is formed, for example, of a plastic, metal, or glass material. The cylindrical member 40 is formed in a cylindrical shape, and includes circular openings formed in opposite ends. The diameter of the cylindrical member 40 may preferably be larger than that of the cells a to be sampled. For the size of the cylindrical member 40, in one example an outer diameter is 4 to 11 mm, inner diameter is 3 to 10 mm, and length is 5 to 10 mm. The size of the cylindrical member 40 is sometimes smaller than that of the example.

Figure 3:
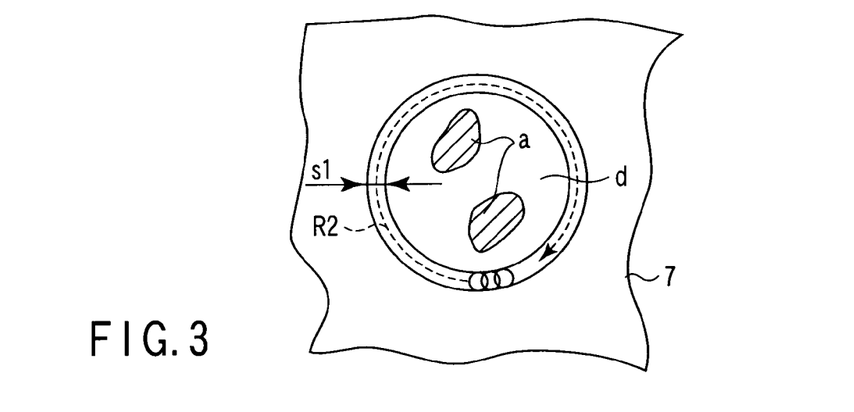
FIG. 3 is a diagram showing a trimming of the cells in first and second embodiments.

When the specimen 7 is larger than the inner diameter of the cylindrical member 40, a specimen portion d including the cells a to be sampled is trimmed. When the shape of the opening of the cylindrical member 40 is circular, the specimen portion d including the sampled cells a in the specimen 7 is trimmed in a circular shape as shown in FIG. 3. When the specimen 7 is smaller than the inner diameter of the cylindrical member 40, the trimming is not necessary.

Figure 4:
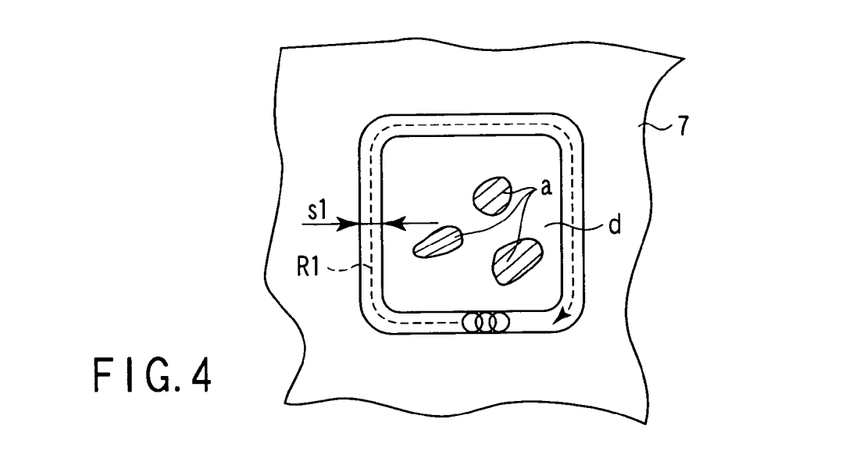
FIG. 4 is a diagram showing a trimming of the cells in the first and second embodiments.

The cylindrical member 40 is not limited to a member including each circular opening, and may also have another shape opening. For example, when the opening of the cylindrical member 40 has a quadrilateral shape, the shape of the specimen portion d to be trimmed is a quadrilateral shape including the cells a to be sampled in the specimen 7 as shown in FIG. 4.

The trimming of the specimen portion d including the cells a to be sampled will be described.

In the variable slit 22 of the UV laser head 21, for example, the circular opening is used. For the variable slit 22, the slit diameter is set, for example, to a spot diameter $s_1$ which is substantially equal to a thickness $s_1$ of a wall of the cylindrical member 40 as shown in FIG. 2.

On the other hand, the LED 26 outputs the red LED light. The LED light is reflected by the dichroic mirror 27, and incident upon the variable slit 25. When the LED light passes through the opening of the variable slit 25, a circular LED light having the spot diameter $s_1$ is shaped.

The specimen 7 is irradiated with the LED light having the spot diameter $s_1$ through the UV image forming lens 24 and objective lens for laser 5. At this time the LED light with the spot diameter $s_1$ transmitted through the dichroic mirror 4 proceeds on the optical axis P of the laser beam outputted from the UV laser head 23. The same position as the irradiation position of the laser beam in the specimen 7 is irradiated with the LED light with the spot diameter $s_1$ in red.

The CCD camera 15 picks up the enlarged image of the specimen 7 to output the image signal. The image processing and stage control apparatus 16 inputs the image signal outputted from the CCD camera 15, image-processes the image signal to acquire the image data, and displays the image data of the specimen 7 irradiated with the red LED light with the spot diameter $s_1$ in the display 17.

The observer observes the specimen 7 displayed in the CCD camera 15 while leaving the specimen portion d, and determines an irradiation route $R_1$ of the laser beam to remove the portion of the specimen 7 around the specimen portion d from the slide glass 8.

When the cylindrical member 40 with the circular opening is used, the irradiation route $R_1$ of the laser beam is circular as shown in FIG. 3. When the cylindrical member 40 having the quadrilateral opening is used, the irradiation route $R_1$ of the laser beam is quadrilateral as shown in FIG. 4.

Next, the UV laser head 23 outputs the laser beam, for example, every shot. The energy of the laser beam is set to such a degree that the outer peripheral portion of the unnecessary specimen portion d on the slide glass 8 is removed from the slide glass 8. It is to be noted that the energy of the laser beam is preferably set to such a degree that the unnecessary portion other than the cells a to be sampled is completely blown off even with slight humidity in ambient environment.

The irradiation route $R_1$ of the specimen 7 is irradiated with the laser beam through the UV image forming lens 24, dichroic mirror 4, and objective lens for laser 5.

The observer confirms the irradiation position of the LED light on the specimen 7 displayed in the display 17 or sees through the eyepiece lens 22 to confirm the irradiation position of the LED light. The observer confirms that the irradiation position of the LED light is on the irradiation route $R_1$ while operating the operation unit 18 such as the keyboard and mouse.

The image processing and stage control apparatus 16 receives the operation command in accordance with the operation of the movement direction and movement amount of the stage 6 from the operation unit 18, and sends the movement control signal of the stage 6 to the stage driving unit 9 in accordance with the operation command.

The stage 6 is moved in the XY direction, for example, every shot of laser beam so that the irradiation position of the LED light on the specimen 7 is disposed on the irradiation route $R_1$. By the movement of the stage 6 in the XY direction, each shot of the laser beam moves on the irradiation route $R_1$ to irradiate the specimen 7.

Each portion of the specimen 7 on the irradiation route $R_1$ irradiated with the laser beam is removed from the slide glass 8. Thereby, as shown in FIG. 3, the specimen portion d including the cells a to be sampled is trimmed in a circular shape. Moreover, as shown in FIG. 4, the specimen portion d including the cells a to be sampled is trimmed in a quadrilateral shape.

It is to be noted that XY coordinate positions of irradiation routes $R_1$, $R_2$ may also be stored in the image processing and stage control apparatus 16 beforehand. That is, after the respective irradiation routes $R_1$, $R_2$ Of the laser beam are determined, the specimen 7 is irradiated with the LED light. The observer operates the operation unit 18 to move the stage 6 in the XY direction, and the LED light is moved along the irradiation routes $R_1$, $R_2$.

At this time, the image processing and stage control apparatus 16 reads the movement direction and amount of the stage 6 from the operation unit 18, and calculates the XY coordinate positions of the stage 6 on the irradiation routes $R_1$, $R_2$ from the movement direction and amount. The image processing and stage control apparatus 16 stores the calculated XY coordinate positions of the irradiation routes $R_1$, $R_2$ in an internal memory.

The image processing and stage control apparatus 16 reads the XY coordinate positions of the respective irradiation routes $R_1$, $R_2$ stored in the internal memory, and sends a movement control signal of the stage 6 to the stage driving unit 9 in accordance with the XY coordinate positions.

The stage 6 automatically moves the irradiation position with the laser beam in the XY direction on the irradiation routes $R_1$, $R_2$. Additionally, the UV laser head 23 outputs one shot of laser beam every predetermined period.

The portions of the specimen 7, on the irradiation routes $R_1$, $R_2$ irradiated with the laser beam are removed from the slide glass 8. Thereby, the specimen portion d including the cells a to be sampled is automatically trimmed in the circular shape as shown in FIG. 3. Moreover, the specimen portion d including the cells a to be sampled is automatically trimmed in the quadrilateral shape as shown in FIG. 4.

When the specimen 7 is irradiated with the laser beam, the broken piece of the specimen 7 is cut off. The cut broken piece flies/scatters, for example, above the slide glass 8.

The air blow 30 blows air above the slide glass 8. The broken piece of the specimen 7 flying/scattering above the slide glass 8 is flied from above the slide glass 8 by the air blown from the air blow 30.

The air suction unit 31 sucks the air, and sucks the broken piece of the specimen 7 flied by the air blowing of the air blow 30.

Thereby, the broken piece of the specimen 7 flying/scattering above the slide glass 8 is removed from the slide glass 8.

The specimen portion d may also be trimmed in the following method.

The specimen 7 is applied with the fluorescence dyestuff beforehand.

The light source for fluorescence excitation 28 emits an ultraviolet light. The ultraviolet light emitted from the light source for fluorescence excitation 28 is transmitted through the UV band pass filter 29 and incident upon the dichroic mirror 11. The ultraviolet light is reflected upwards by the dichroic mirror 11, and the specimen 7 is irradiated with the light through the objective lens for observation 10. The fluorescence dyestuff applied to the specimen 7 is excited and emits.

The fluorescence from the specimen 7 is transmitted through the dichroic mirror 11 and UV barrier filter 12 from the objective lens for observation 10, and formed into the image by the image forming lens 13.

The CCD camera 15 picks up the enlarged image and fluorescence of the specimen 7 to output the image signal. The image processing and stage control apparatus 16 inputs the image signal outputted from the CCD camera 15, image-processes the image signal to acquire the image data, and displays the image data of the specimen 7 emitting the fluorescence in the display 17.

Additionally, the image and fluorescence of the specimen 7 are reflected by the mirror 19, and pass through the relay lenses 20 and UV cut filter 21 to be incident upon the eyepiece lens 22. Thereby, the observer sees through the eyepiece lens 22 to visually observe the enlarged image of the specimen 7 emitting the fluorescence.

The observer observes the enlarged image of the specimen 7 displayed in the display 17, or sees through the eyepiece lens 22 to observe the enlarged image and fluorescence of the specimen 7. The observer can observe the enlarged image and fluorescence of the specimen 7 to determine the cells a to be sampled from the specimen 7.

Since the fluorescence dyestuff applied to the specimen 7 emits the light, as compared with the use of the visible ray, the cells a to be sampled is further easily determined. The image can also be recognized using a computer to automatically select the cells a to be sampled.

Next, a procedure of leaving only the cells a to be sampled and removing other cells from the specimen d including the cell a to be sampled.

Figure 8:
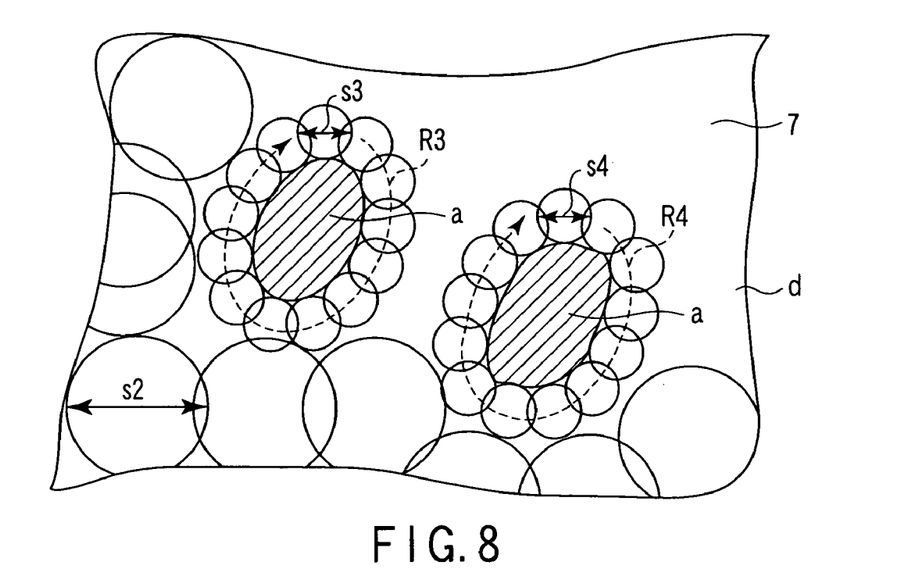
FIG. 8 is a diagram showing irradiation of an unnecessary cells with laser in the first and second embodiments.

For the variable slit 25 maximizes the diameter of the opening. The variable slit 25 enlarges the spot diameter of the laser beam outputted from the UV laser head 23. As shown in FIG. 8, the cells a detached from the cells a to be sampled are irradiated with the laser beam which has a large spot diameter $s_2$.

Next, the variable slit 25 reduces the diameter of the opening. The periphery of the cells a to be sampled are irradiated with the laser beam having a small spot diameter $s_3$ more carefully, that is, correctly along the periphery of the cells a. Only the cells a to be sampled are left.

Next, the cylindrical member 40 shown in FIG. 2 is prepared. An adhesive 41 is applied to one opening of the cylindrical member 40. The cylindrical member 40 is bonded to the substrates such as the slide glass 8 using grease, paraffin, and various adhesives which are not influenced by the solution for stripping or extracting. Moreover, a disposable thick seal or cylindrical member which is coated with the adhesive beforehand may also be used.

The cylindrical member 40 is disposed vertically to the upper surface of the slide glass 8 while one operation is directed downwards. When the cylindrical member 40 is disposed on the upper surface of the slide glass 8, the specimen portion d including the cells a are inserted into one opening.

Next, the cylindrical member 40 is lightly pressed against the slide glass 8 side. This secures the adhesion of the cylindrical member 40 to the slide glass 8. When the adhesive 41 hardens, a liquid-tight container is formed by the cylindrical member 40 and slide glass 8. The cylindrical member 40 and slide glass 8 are removed from the stage 6.

Figure 5:
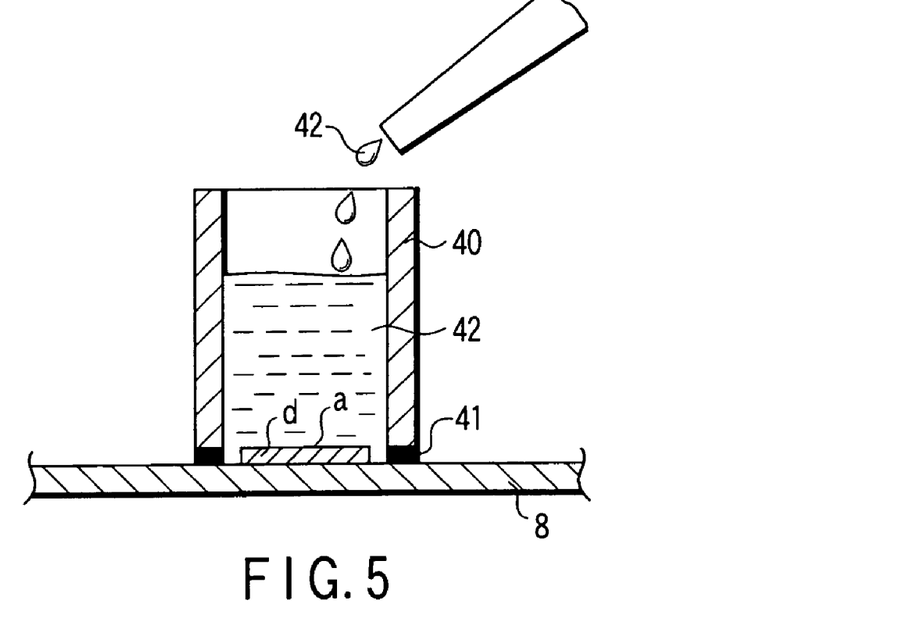
FIG. 5 is a diagram showing an injection of a stripping agent in the first and second embodiments.
Figure 6:
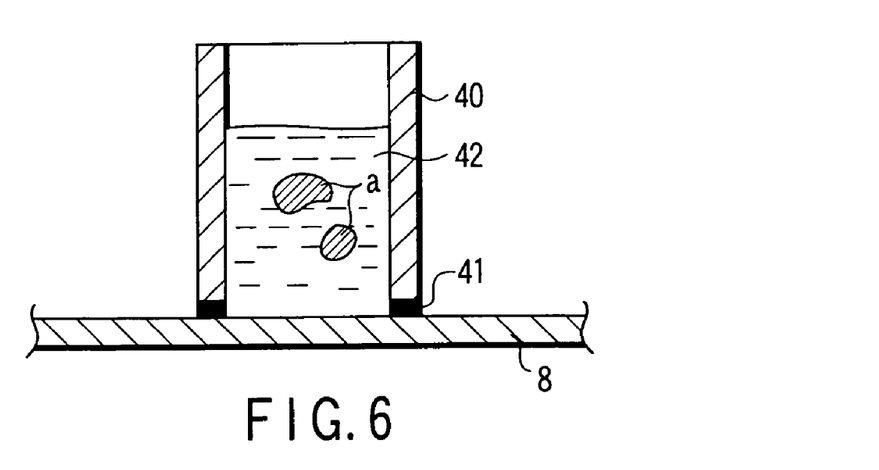
FIG. 6 is a diagram showing a stripped state of the cells in the first and second embodiments.

Next, a stripping agent 42 is injected into the container formed by the cylindrical member 40 and slide glass 8 as shown in FIG. 5. Examples of the stripping agent 42 include organic solvents such as xylene and surfactants. The stripping agent 42 promotes the stripping of the cells a from the slide glass 8. FIG. 6 shows the cells a stripped from the slide glass 8. The stripped cells a are floated in the stripping agent 42.

Next, the cells a floating in the stripping agent 42 is sucked together with the stripping agent 42 by a dropper. The cells a sucked by the dropper is transferred into another new container. As a result, the sampling of the cells a ends.

In this manner, according to the first embodiment, the method comprises: inserting the specimen portion d smaller than the inner diameter of the opening of the cylindrical member 40 into the opening and disposing the cylindrical member 40 on the slide glass 8; forming a portion between the cylindrical member 40 and slide glass 8 by the adhesive 41 in the liquid-tight manner; injecting the stripping agent 42 into the container formed by the cylindrical member 40 and slide glass 8; and stripping the cells a to be sampled from the slide glass 8 and floating the cells in the stripping agent 42 to sample the cells.

Therefore, the cells a to be sampled included in the specimen 7 can securely be sampled. This prevents the position of the cells a from being unknown as in the related art. The cells a cannot be lost. The foreign particles such as dust can securely be prevented from being mixed in the sampled cells a.

In the first embodiment, since the specimen 7 is first laid on the slide glass 8, any special thin film plate or film is not used as in the related art. The operation of attaching the specimen 7 to the thin film plate or film can be eliminated. Thereby, in the first embodiment, the sampling operation of the cells a can be simplified and efficiently performed. Additionally, this is economically advantageous.

In the above-described first embodiment, since the transparent cap for sampling the cells in the related art is not used, the spot diameter of the laser beam can be reduced. Therefore, even when the cell a to be sampled is micro, the cells a to be sampled is left, and the other cells can be irradiated with the laser beam.

In the first embodiment, special materials such as a transfer film are not used. Therefore, a trouble of operation is saved, and expenses of consumables can be saved.

In general, when the function of the cell or the gene included in the cells is analyzed, the mixture of the cells other than the targeted cells or the gene is requested to be reduced to enhance the purity of the sample. Moreover, since it takes much time to select and acquire the necessary cells from the specimen cut piece, there has been a demand for efficiency in acquiring the cells.

On the other hand, according to the first embodiment, since the unnecessary cells are removed and only a large number of necessary cells can be acquired at once, it is possible to efficiently acquire the high-purity sample.

The above-described embodiment comprises: injecting the stripping agent 42 into the cylindrical member 40; and stripping the cells a to be sampled from the slide glass 8 and floating the cells to sample the cells. This cell sampling method is effective in a research in which the shape of the nucleus of the cells a need to be held as completely as possible, for example, analysis of a flow cytometry.

The first embodiment can appropriately be modified and carried out.

For example, the adhesive 41 is not necessarily used between the cylindrical member 40 and slide glass 8. When the adhesive 41 is not used, for example, the grease may thinly be applied to the opening of the cylindrical member 40. This may prevent the stripping agent 42 from leaking between the cylindrical member 40 and slide glass 8.

The material of the cylindrical member 40 is not limited to glass, and other materials such as plastic and metal can also be used.

Figure 9:
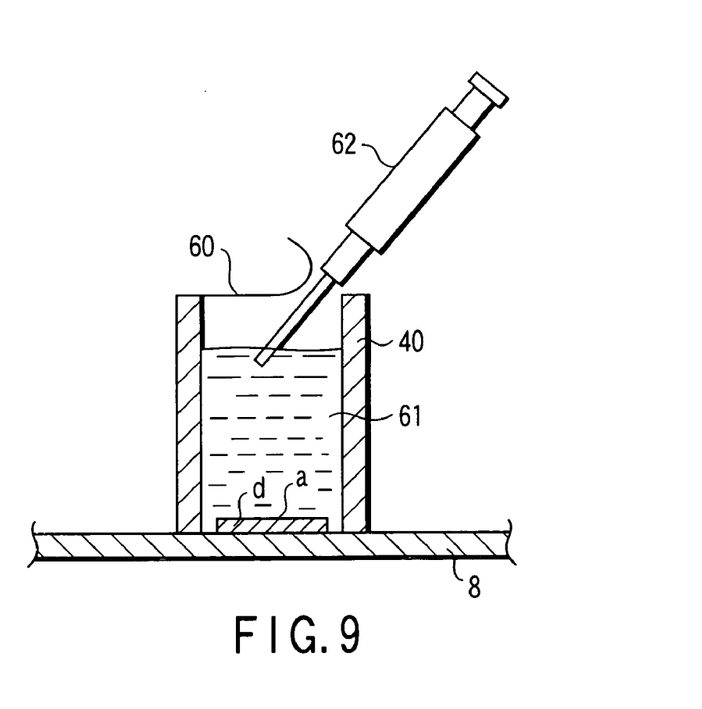
FIG. 9 is a diagram showing one example of a sampling method of the cells in the first and second embodiments.

Moreover, as shown in FIG. 9, a transparent film 60 formed by a thin resin can also be attached to one opening of the cylindrical member 40 for use. In this case, a stripping agent/extract agent 61 is injected/recovered, for example, using a dropper, pipette, and syringe 62.

Next, the transparent film 60 is stripped, and the stripping agent/extract agent 61 is injected into the cylindrical member 40.

Next, the stripping agent/extract agent 61 is reacted in a sealed state by the transparent film 60.

Thereafter, the transparent film 60 is stripped, and the solution is recovered, for example, by the dropper, pipette, and syringe 62.

This can prevent the mixture of the foreign particles into the cylindrical member 40.

It has been described that the first embodiment is effective in the analysis such as the flow cytometry. On the other hand, there are researches such as analysis of nucleic acid (DNA, RNA) and protein. This research does not require the stripping of the cells a from the slide glass 8.

That is, as shown in FIG. 2, the cylindrical member 40 is bonded/fixed onto the slide glass 8. Next, the slide glass 8 is removed from the stage 6.

Next, as shown in FIG. 5, instead of the stripping agent 42, a solution for directly extracting the sample to be sampled such as the nucleic acids and protein from the cells a is injected into the cylindrical member 40. Examples of the solution include a commercially available solution such as a nucleic acid extract kit.

When the samples such as the nucleic acid (DNA, RNA) and protein are eluted in the solution, the samples eluted in the solution are sucked with the dropper and transferred into another new container in the same manner as in the first embodiment.

For example, the nucleic acid (DNA, RNA) and protein sampled in this manner can be used to analyze the nucleic acid (DNA, RNA) and protein.

Next, a second embodiment of the present invention will be described. It is to be noted that the same components as those of FIG. 1 are denoted with the same reference numerals, and the detailed description thereof is omitted.

Figure 7:
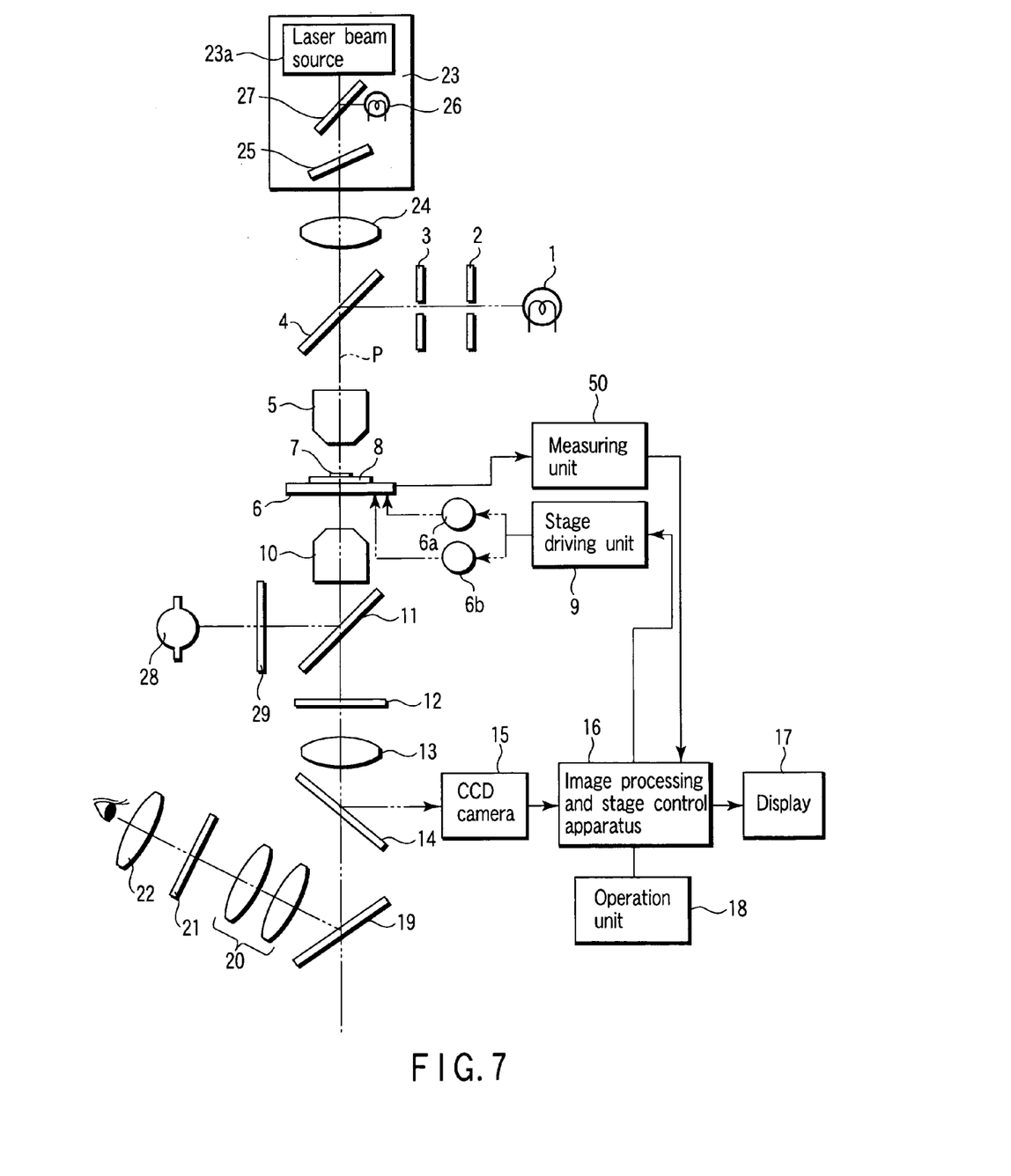
FIG. 7 is a constitution diagram of the inverted microscope for use in the second embodiment of the cell acquiring method of the present invention.

FIG. 7 is a constitution diagram of the inverted microscope for use in the cell acquiring method of the present invention. The UV laser head 23 outputs the laser beam having the wavelength of the ultraviolet region. The laser beam outputted from the UV laser head 23 is set to the energy for leaving the cells a to be sampled among a plurality of cells included in the specimen 7 and damaging properties of the unnecessary specimen portion other than the cells a to be sampled. The damaging of the properties of the unnecessary specimen portion means that the nucleic acid is fractionated to change the basic properties of the nucleic acid or cell.

The stage 6 includes a measuring unit 50. The measuring unit 50 measures an XY coordinate which moves in the XY direction of the stage 6, and outputs an XY coordinate measuring signal.

The image processing and stage control apparatus 16 is inputted the XY coordinate measuring signal outputted from the measuring unit 50, and calculates the irradiation position of the laser beam with which the specimen 7 is irradiated from the XY coordinate measuring signal.

The image processing and stage control apparatus 16 image-processes the image signal outputted from the CCD camera 15 to acquire the image data of the specimen 7, and superimposes image data of a colored display portion indicating the irradiation position of the laser beam upon the image data. The colored display portion is preferably, for example, in red.

The image processing and stage control apparatus 16 superimposes the image data of the specimen 7 upon the image data of the colored display portion indicating the irradiation position of the laser beam to display the data in the display 17.

Next, the sampling method of the cell a existing in the specimen 7 will be described.

In the same manner as in the first embodiment, the observer observes the enlarged image of the specimen 7 displayed in the display 17 or sees through the eyepiece lens 22 to observe the enlarged image of the specimen 7 to determine each cells a to be sampled from the specimen 7, for example, shown in FIG. 8.

Next, each cells a to be sampled in the specimen 7 are left, and the other cells are irradiated with the laser beam.

The cells detached from the cells a to be sampled are irradiated with the laser beam with the large spot diameter $s_2$.

Next, the variable slit 25 forms the small spot diameter $s_3$, and irradiates the periphery of the cells a to be sampled carefully, that is, correctly along the periphery of the cells a to leave only the cells a to be sampled.

In the first embodiment, the laser spot diameter is adjusted by the variable slit 25, but in the second embodiment, the laser energy may only be supplied to fractionate the nucleic acid of the unnecessary cell. The laser energy for fractionating the nucleic acid is smaller than the energy for removing the whole cell. Thereby, instead of the UV laser head 23, the mercury lamp is used to fractionate the nucleic acid of the unnecessary cell, and the basic properties of the nucleic acid or cell can be damaged. Moreover, the objective lens for laser 5 can be changed to a lens with a low magnification to enlarge the laser spot diameter.

The objective lens for laser 5 is changed to the magnification such as about five times.

Moreover, the measuring unit 50 measures the XY coordinate which moves in the XY direction of the stage 6, and outputs the XY coordinate measuring signal.

The image processing and stage control apparatus 16 inputs the XY coordinate measuring signal outputted from the measuring unit 50, and calculates the irradiation position of the laser beam with which the specimen 7 is irradiated from the XY coordinate measuring signal.

The image processing and stage control apparatus 16 image-processes the image signal outputted from the CCD camera 15 to acquire the image data of the specimen 7, and superimposes the image data upon the image data of the colored display portion indicating the irradiation position of the laser beam, for example, in red.

The image processing and stage control apparatus 16 superimposes the image data of the specimen 7 upon the image data of the colored display portion indicating the irradiation position of the laser beam to display the data in the display 17.

The observer operates the operation unit 18, confirms the image of the specimen 7 displayed in the display 17 and the colored display portion indicating the irradiation position of the laser beam, and moves the irradiation position of the laser beam with the spot diameter $s_2$ to the peripheral portion of each cell a every shot.

The specimen 7 around each cell a is irradiated with the laser beam with the spot diameter $s_2$. It is to be noted that FIG. 8 does not show all the irradiation positions of the laser beam with the spot diameter $s_2$.

For the portion of the specimen 7 irradiated with the laser beam with the spot diameter $s_2$, when the nucleic acid is fractionated, the basic properties of the nucleic acid or cell are damaged.

Next, for the variable slit 22 of the UV cut filter 21, the diameter of the circular opening is set, for example, to the slit width $S_3$ smaller than the cells a as shown in FIG. 8. Thereby, the spot diameter of the laser beam with which the specimen 7 is irradiated is $s_3$.

It is to be noted that the objective lens for laser 5 is changed to a high magnification such as about five times, and an ND filter may also be disposed before the objective lens for laser 5.

The observer observes the specimen 7 displayed in the display 17 to determine irradiation routes $R_3$, $R_4$ of the laser beam for leaving each cells a and damaging the properties of the ambient specimen 7 disposed adjacent to each cells a.

The observer confirms the image of the specimen 7 displayed in the display 17 and the colored display portion indicating the irradiation position of the laser beam, and operates the operation unit 18 so as to dispose the irradiation position of the laser on the irradiation route $R_3$ or $R_4$.

The image processing and stage control apparatus 16 receives the operation command in accordance with the operation of the movement direction and movement amount of the stage 6 from the operation unit 18, and sends the movement control signal of the stage 6 to the stage driving unit 9 in accordance with the operation command.

Thereby, the stage 6 is moved in the XY direction, for example, every shot of laser beam so as to dispose the irradiation position on the irradiation route $R_1$ or $R_3$.

When the laser beam is shot from the UV laser head 23, for example, every shot, the irradiation route $R_3$ is irradiated with the laser beam passed through the UV image forming lens 24, dichroic mirror 4, and objective lens for laser 5, and subsequently the irradiation route $R_4$ is irradiated. It is to be noted that the irradiation route $R_4$ and then the irradiation route $R_3$ may be irradiated with the laser beam.

The energy of the laser beam is set to such an extent that the properties of the surrounding specimen 7 disposed adjacent to each cell a are damaged. Therefore, for the portions of the specimen 7 on the respective irradiation routes $R_3$, $R_4$ irradiated with the laser beam, when the nucleic acid is fractionated, the basic properties of the nucleic acid or cell are damaged.

It is to be noted that the XY coordinate positions of the irradiation routes $R_3$, $R_4$ may also be stored in the image processing and stage control apparatus 16 beforehand. That is, after the irradiation routes $R_3$, $R_4$ of the laser beam are determined, the observer operates the operation unit 18 to move the stage 6 in the XY direction, and moves the colored display portion indicating the irradiation position of the laser beam along each of the irradiation routes $R_3$, $R_4$.

At this time, the image processing and stage control apparatus 16 reads the movement direction and amount of the stage 6 from the operation unit 18, and calculates the XY coordinate positions of the stage 6 in the irradiation routes $R_3$, $R_4$ from the movement direction and amount. The image processing and stage control apparatus 16 stores the calculated XY coordinate positions on the irradiation routes $R_3$, $R_4$ in the internal memory.

The image processing and stage control apparatus 16 reads the XY coordinate positions for each of the irradiation routes $R_3$, $R_4$ stored in the internal memory, and sends the movement control signal of the stage 6 to the stage driving unit 9 in accordance with the XY coordinate positions.

The stage 6 automatically moves the irradiation position with the laser beam in the XY direction for each of the irradiation routes $R_3$, $R_4$. Additionally, the UV laser head 23 outputs one shot of laser beam every predetermined period.

Thereby, the portions of the specimen 7 on the irradiation routes $R_3$, $R_4$ are automatically irradiated with the laser beam, and the basic properties of the nucleic acid or cell are damaged the fractionation of the nucleic acid in the cell.

Next, the cylindrical member 40 shown in FIG. 2 is prepared in the same manner as in the first embodiment. The cylindrical member 40 is bonded/fixed onto the slide glass 8.

Next, the solution for extracting the sample such as the nucleic acid (DNA, RNA) and protein from the cells a is injected into the cylindrical member 40 as shown in FIG. 5.

When the sample such as the nucleic acid (DNA, RNA) and protein is eluted in the solution, the sample is sucked with the dropper and transferred into new another container.

On the other hand, when the cells a are stripped from the slide glass 8, the cylindrical member 40 is bonded/fixed onto the slide glass 8 by the adhesive 41 as shown in FIG. 2.

Next, the stripping agent 42 is injected into the container formed by cylindrical member 40 and slide glass 8 as shown in FIG. 5. The stripping agent 42 promotes the stripping of the cells a from the slide glass 8 as shown in FIG. 6.

Next, the cells a floating in the stripping agent 42 is sucked with the dropper together with the stripping agent 42. The cell a sucked with the dropper is transferred into new another container. As a result, the sampling of the cell a ends.

In this manner, according to the second embodiment, the unnecessary specimen portion d other than the cells a to be sampled in the specimen 7 are irradiated with the laser beam, the nucleic acid of the unnecessary specimen portion d is fractionated, and the basic properties of the nucleic acid or cell are changed.

Thereafter, the solution for extracting the samples such as the nucleic acid (DNA, RNA) and protein from the cells a is injected into the cylindrical member 40, and the samples such as nucleic acid (DNA, RNA) and protein are eluted. Moreover, the stripping agent 42 is injected into the container formed by the cylindrical member 40 and slide glass 8, and the cells a to be sampled is stripped from the slide glass 8, floated in the stripping agent 42, and sampled.

In this manner, in the second embodiment, the nucleic acid of the cells of the unnecessary specimen portion d is irradiated with the laser beam and fractionated to change the basic properties of the nucleic acid or cell. Therefore, the embodiment is effective mainly in extracting the samples such as the nucleic acid (DNA, RNA) and protein from the raw specimen 7.

The raw specimen contains moisture. When the raw specimen 7 is irradiated with the laser beam having a large energy, the specimen 7 cannot be cut because of the boiled moisture in the specimen 7.

On the other hand, the energy of the laser beam in the second embodiment is an energy necessary for fractionating the nucleic acid of the unnecessary specimen portion d to damage the basic properties of the nucleic acid or cell. For the energy of the laser beam, as an experiment result, for example, in the fractionation of DNA, an energy of 0.075 mJ is obtained at a wavelength of 266 nm in a square area of 60 µm sides. It is to be noted that even with the energy of the laser beam smaller than 0.075 mJ, the nucleic acid can be fractionated to change the basic properties of the nucleic acid or cell.

When the properties of the unnecessary specimen portion other than the cells a necessary for the sampling are changed, first the unnecessary specimen portion d around each cell a is irradiated with the laser beam having the large spot diameter $s_2$, and next the unnecessary surrounding specimen portion d disposed adjacent to each cell a is irradiated with the laser beam having the small spot diameter $s_3$. This can reduce the number of laser shots with which the unnecessary specimen portion d is irradiated. The properties of the unnecessary specimen portion d in a broad region can be changed in a short time.

When the unnecessary specimen portion d is flied from the slide glass 8 as in the first embodiment, in general, the objective lens for laser 5 with a magnification of about 50 times is used. On the other hand, in the second embodiment the objective lens for laser 5 with a magnification of about five times may also be used. Thereby, in the second embodiment, as compared with the use of the objective lens for laser 5 with the magnification of 50 times, the spot region of the laser beam can be enlarged 100 times.

Since the properties of the cells of the unnecessary specimen portion d are damaged, the broken pieces of the specimen 7 irradiated with the laser beam are not flied/scattered. Thereby, the air blow 30 and air suction unit 31 are unnecessary.

In the display 17, the image data of the colored display portion, for example, in red indicating the irradiation position of the laser beam is superimposed and displayed upon the image data of the specimen 7. The observer can confirm the image of the display 17 while the specimen 7 is irradiated with the laser beam. Thereby, the periphery disposed adjacent to the cells a to be sampled and other unnecessary specimen portion d can securely be changed in properties.

In the second embodiment, the energy of the laser beam is set to such an extent that the properties of the cells are damaged. As a light source, for example, the mercury lamp or Xenon lamp may also be used. Even when the cell is irradiated with the light emitted from the mercury lamp or Xenon lamp, it is possible to fractionate the nucleic acid and to change the basic properties of the nucleic acid or cell.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. A method of collecting a specific portion of a specimen including a plurality of cells comprising:
    laying the specimen on a substrate;
    irradiating the specimen with a laser beam in a region other than the specific portion to be collected so as to remove an unnecessary portion of the specimen from the substrate;
    abutting one of opposite ends of a cylindrical member including openings in the opposite ends to contact the substrate in a fluid-tight state such that the specific portion to be collected is positioned inside the cylindrical member;
    introducing a stripping agent inside the cylindrical member abutted against the substrate so as to strip the specific portion to be collected from the substrate and cause the specific portion to be collected to float in the stripping agent; and
    collecting the specific portion from the stripping agent.

2. The method according to claim 1, further comprising setting an energy of the laser beam to such an intensity that the unnecessary portion of the specimen is completely blown/flied from the substrate.

3. The method according to claim 1, further comprising setting an energy of the laser beam to such an intensity that the unnecessary portion of the specimen is burned or crushed.

4. The method according to claim 1, wherein the irradiating of the unnecessary portion of the specimen with the laser beam to remove the unnecessary portion of the specimen from the substrate comprises:
    spraying air to the specimen to fly a broken piece from the specimen; and
    sucking the broken piece flied from the specimen.

5. The method according to claim 1, further comprising setting a wavelength of the laser beam to an ultraviolet region.

6. The method according to claim 1, wherein the cylindrical member is formed of one of glass, metal, and plastic.

7. The method according to claim 1, wherein the cylindrical member includes a thin film formed out of resin which is attached to a first one of the openings that is opposite to a second one of the openings which is in contact with the substrate and, when the stripping agent is introduced, the thin film is temporarily stripped.

8. The method according to claim 1, further comprising fixing the cylindrical member onto the substrate by an adhesive.

9. The method according to claim 1, further comprising sealing a gap between the cylindrical member and substrate by grease applied onto the substrate.

10. The method according to claim 1, wherein the stripping agent is an organic solvent.

11. The method according to claim 10, wherein the stripping agent is xylene.

12. The method according to claim 1, wherein collecting the specific portion from the stripping agent comprises:
    sucking the specific portion in the stripping agent with a dropper, pipette, or syringe; and
    transferring the specific portion in the dropper, pipette, or syringe to a container.

13. The method according to claim 1, further comprising:
    applying a fluorescence dyestuff to the specimen to dye the specific portion to be collected;
    irradiating the specimen with an ultraviolet light cause the fluorescence dyestuff to emit light; and
    observing a portion of the specimen that has emitted the light to determine the specific portion to be collected.

14. The method according to claim 1, further comprising:
    providing a microscope which enlarges an image of the specimen and a laser head which outputs the laser beam, such that an optical axis of the microscope agrees with an optical axis of the laser beam outputted from the laser head;
    outputting an indexing light, from a light source for indexing, on a same axis as the optical axis of the laser beam outputted from the laser head;
    picking up the image of the specimen enlarged by the microscope and the indexing light with which the specimen is irradiated, by an image pickup apparatus to display, the image of the specimen and the indexing light by a display apparatus; and
    observing the image of the specimen and the indexing light displayed by the display apparatus to scan the laser beam on the specimen so as to remove the unnecessary portion of the specimen from the substrate.

* * * * *